United States Patent [19]

Coppler et al.

[11] Patent Number: 5,305,231
[45] Date of Patent: Apr. 19, 1994

[54] MULTIPLE K FACTOR, SELECTABLE GAS DETECTOR

[75] Inventors: Mark J. Coppler, Kennedy Township, Butler County; Robert L. Novack, Cranberry Township, Butler County; John E. Tozier, Allegheny County; Peter M. Noble, Adams Township, Butler County, all of Pa.

[73] Assignee: Bacharach, Inc., Pittsburgh, Pa.

[21] Appl. No.: 835,627

[22] Filed: Feb. 13, 1992

[51] Int. Cl.⁵ .............................................. G06F 15/46
[52] U.S. Cl. ................................................... 364/497
[58] Field of Search ....................... 364/571.01–571.08, 364/497, 498, 499; 73/1 G, 23.2, 23.21, 31.06, 25.03; 422/98; 204/408, 412, 432

[56] References Cited

U.S. PATENT DOCUMENTS

| | | | |
|---|---|---|---|
| 4,464,653 | 8/1984 | Winner | 73/23.2 X |
| 4,476,706 | 10/1984 | Hadden et al. | 73/1 G |
| 4,481,804 | 11/1984 | Eberhard et al. | 73/1 G |
| 4,541,988 | 9/1985 | Tozier et al. | 422/94 |
| 4,542,640 | 9/1985 | Clifford | 73/23 |
| 4,555,930 | 12/1985 | Leach et al. | 73/1 G X |
| 4,567,475 | 1/1986 | Bukowiecki et al. | 340/634 |
| 4,642,296 | 2/1987 | Hubner | 73/23.2 X |
| 4,664,886 | 5/1987 | Novack et al. | 422/94 |
| 4,670,405 | 6/1987 | Stetter et al. | 436/151 |
| 4,818,348 | 4/1989 | Stetter | 204/1 G |
| 4,847,783 | 7/1989 | Grace et al. | 364/497 |
| 4,852,384 | 8/1989 | Woolbert et al. | 73/1 G |
| 5,007,283 | 4/1991 | Ambos | 73/1 G |
| 5,025,653 | 6/1991 | Schuldt | 73/1 G |
| 5,055,269 | 10/1991 | Palumbo et al. | 422/96 |
| 5,184,500 | 2/1993 | Krcma et al. | 73/23.2 |

Primary Examiner—Kevin J. Teska
Attorney, Agent, or Firm—Webb, Burden, Ziensenheim & Webb;

[57] ABSTRACT

A gas detector apparatus for determining the concentration of a selected one of a plurality of predetermined gases includes a gas sensor which generates a gas output signal related to the concentration of the selected predetermined gas in the gas sample. A K factor storage associated with the gas sensor stores at least one K factor, unique to and generated by using the gas sensor, for each of the plurality of predetermined gases. A processor, in response to a selected gas control signal, selects the K factor or factors from the K factor storage for the selected gas and, in accordance with a predetermined process stored therein, calculates a concentration signal representing the concentration of the selected gas in the gas sample.

51 Claims, 5 Drawing Sheets

MULTIPLE K FACTOR, SELECTABLE GAS DETECTOR

BACKGROUND OF THE INVENTION

1. Field Of The Invention

This invention relates to gas detectors and, more particularly, to a gas detecting apparatus which can selectively monitor one of a plurality of gases in a sampled atmosphere.

2. Description Of The Prior Art

It is often desirable to measure the concentration of gas levels, such as oxygen or combustible gases, in a sampled or confined atmosphere. Low levels of oxygen present a danger to human life. For combustible gases, typically one is concerned with the lower explosive limit, the lowest concentration at which a flame will propagate or burn when the gas is exposed to an open flame or spark. In addition, inert and other gases also may pose a hazard as they displace oxygen in the air.

A number of methods have been developed for detecting specific gases. For example, the use of catalytic sensors to measure the concentration of combustible gases is well known. In such a sensor, a resistive element is coated with a catalytic material which reacts when contacted with a particular gas. A current passing through the resistive element heats the catalytic coating to a desired operating temperature and as the gas and oxygen contact the catalytic coating, it chemically reacts thereupon and adds heat to the resistive element. This additional heat changes the resistance of the coated element, a change that can be detected electrically in various known ways. In a common arrangement, a catalytic sensor, combining an active element in series with a reference element, is provided in one branch of a Wheatstone bridge. Voltage imbalances in the Wheatstone bridge are measured and provide a reading of the concentration of the gas contacting the sensor. Other known sensors for detecting a combustible gas include metal oxide semiconductor sensors in which the conductivity of the material changes when contacted by a particular gas. This change in conductivity can also be measured electrically to provide a direct reading of the concentration of the gas.

For many known sensors, the electrical signal generated when the sensor is contacted by a particular gas is proportionally related to the gas concentration. The slope of a plot of gas concentrations versus electrical activity in the sensor is often referred to as a sensitivity for the sensor. The ratio of the sensitivity of a sensor to different gases is sometimes referred to as a K factor, conversion factor, scaling factor or multiplier. Once the K factor for a gas is calculated or determined empirically, unknown concentrations of gas can be determined by measuring the electrical response of the sensor, such as a voltage change, and multiplying that response by the K factor for the sensor for that gas. This method allows the user to measure concentrations of various gases with an instrument that has been calibrated with a single gas, e.g., measuring hydrogen with an instrument calibrated on methane. While it is possible to use several K factors over a range of electrical activities, representing non-linearities in the gas sensor response, it is more common to use a single K factor for the entire range of operation of the sensor.

Gas sensors are typically "tuned" or constructed to react with and generate electrical responses relative to a single, predetermined gas. Measurements involving pluralities of unknown gases often use multiple sensors, each of which is tuned to a particular gas, or use complicated arrays or networks of sensors in conjunction with analysis equipment to generate readings for various gases. An example of a prior art arrangement for detecting the level of a combustible gas, the level of oxygen, and the displacement of air by an unknown third gas is shown in U.S. Pat. No. 4,664,886. Other arrangements for detecting multiple gases are shown in U.S. Pat. Nos. 4,481,804, 4,542,640, 4,567,475, 4,670,405, 4,818,348, 4,847,783, 5,007,283, and 5,025,653.

It is often desired to measure one of a plurality of gases, such as 10-15 gases, in a sample atmosphere. The prior art arrangements require the sample atmosphere to be monitored by a plurality of expensive gas sensors, or require that a gas sensor be changed each time a different gas present in the sample atmosphere is to be detected.

It is an object of the present invention to provide a gas detecting apparatus which can readily and selectively measure one of a plurality of gases at unknown concentration levels. It is an object of the present invention to provide such a gas detector which is easy to use, easy to select from one gas to another, and which is not overly complicated or expensive to manufacture. It is also an object of the present invention to provide such an arrangement without using a plurality of separate gas sensors.

SUMMARY OF INVENTION

Accordingly, we have invented a gas detecting apparatus for determining the concentration, in a gas sample, of a selected one of a plurality of predetermined gases. The apparatus includes a sampling means for obtaining the gas sample and a gas sensing means connected to the sampling means for generating a gas output signal related to the concentration of the selected predetermined combustible gas. The apparatus also includes a drive means for supplying controlled electrical power to the gas sensing means and a K factor storage means associated with the gas sensing means for storing at least one K factor, unique to and generated by using the gas sensing means, for each of the plurality of predetermined gases. A gas selector means is provided for generating a selected gas signal representing the particular selected gas to be detected. The apparatus also includes a processor means for, in response to the selected gas signal and the gas output signal, selecting the K factor or factors from the K factor storage means for the selected gas and, in accordance with a predetermined process stored in the processor means, calculating a concentration signal representing the concentration of the selected gas in the sample. Finally, a display means responsive to the concentration signal displays the concentration of the detected gas in the gas sample.

In a preferred arrangement, the gas sensing means is a combustible gas sensor generating a combustible gas output signal. The apparatus can also include an oxygen sensing means connected to the sampling means for generating an oxygen output signal proportional to the concentration of oxygen in the gas sample and a mode selector means for generating a mode signal representing the mode of operation of the apparatus, selectable between at least an oxygen detection mode and a combustible gas detection mode. The processor means can generate concentration signals representing either the oxygen concentration or the combustible gas concentration in the gas sample. The oxygen sensing means can be an electrochemical oxygen sensor and the combustible gas sensing means can be a catalytic combustible sensor. The catalytic combustible gas sensor can have an active element and reference element whose resistance varies as a function of temperature, with the sensor forming one branch of a Wheatstone bridge network and with electrical imbalances in the bridge generating the combustible gas output signal. The drive means can adjust the electrical power supply to the catalytic combustible gas sensor to maintain the operating temperature of at least the active element at a predetermined constant level. The apparatus can also include an alarm for indicating when the concentration of the combustible gas exceeds a predetermined level or when the concentration of oxygen falls below a predetermined level.

Preferably, the processor means is a microprocessor based digital controller and the combustible gas output signal, selected gas signal, oxygen output signal and mode signal are analog signals which are supplied to a multiplexer which supplies these signals to an analog-to-digital converter in the digital controller. The K factor storage means is preferably a digital memory means capable of supplying its stored K factor information directly to a microprocessor in the digital controller. The digital memory means can be an electrically erasable programmable read only memory. The gas selector means and the mode selector means can each be formed of a series resistance network connected to a source of voltage and include a plurality of contacts positioned between adjacent resistors in the resistance network and connected to a multi-position selector switch having at least as many positions as the number of predetermined combustible gases or modes, respectively, to be selected.

It is preferred that the combustible gas sensing means and the K factor storage means both be mounted on a common support. The K factors stored in the K factor storage means can be generated in advance for a particular combustible gas sensing means in accordance with the following steps: (a) applying electrical power to said gas sensing means; (b) measuring the combustible gas output signal when clean air is applied to said combustible gas sensing means; (c) applying a first of said predetermined combustible gases in a known concentration to said combustible gas sensing means and measuring the combustible gas output signal generated thereby; (d) calculating the K factor of said first combustible gas based upon the combustible gas output signals generated in steps (b) and (c) above and the known concentration of said first combustible gas; and (e) repeating steps (b)-(d) for each of the remaining of said predetermined combustible gases. It is advantageous to select one of the combustible gases as a reference and assign to it a K factor of 1, with the K factors for each of the remaining combustible gases calculated with respect to the reference gas. The concentration signal for the combustible gases can be presented as a percent of the lower explosive limit of the combustible gas in the gas sample.

An advantage of the present invention is that each combustible gas sensor can be uniquely tuned by generating K factors from actual measurements on that particular sensor. No fixed set of precalculated K factors are stored in the gas detecting apparatus and used in future measurements with any combustible gas sensor. Therefore, operating variations from sensor to sensor can be minimized or eliminated by applying test gases to each combustible gas sensor, generating K factors for each combustible gas sensor for each combustible gas, and thereafter using a particular set of K factors for a particular combustible gas sensor. By packaging the combustible gas sensor with the K factor storage means, each such package can be calibrated in a central location and used in any detector with only the normal zero and span adjustments.

DESCRIPTION OF THE PREFERRED EMBODIMENTS

Figure 1:
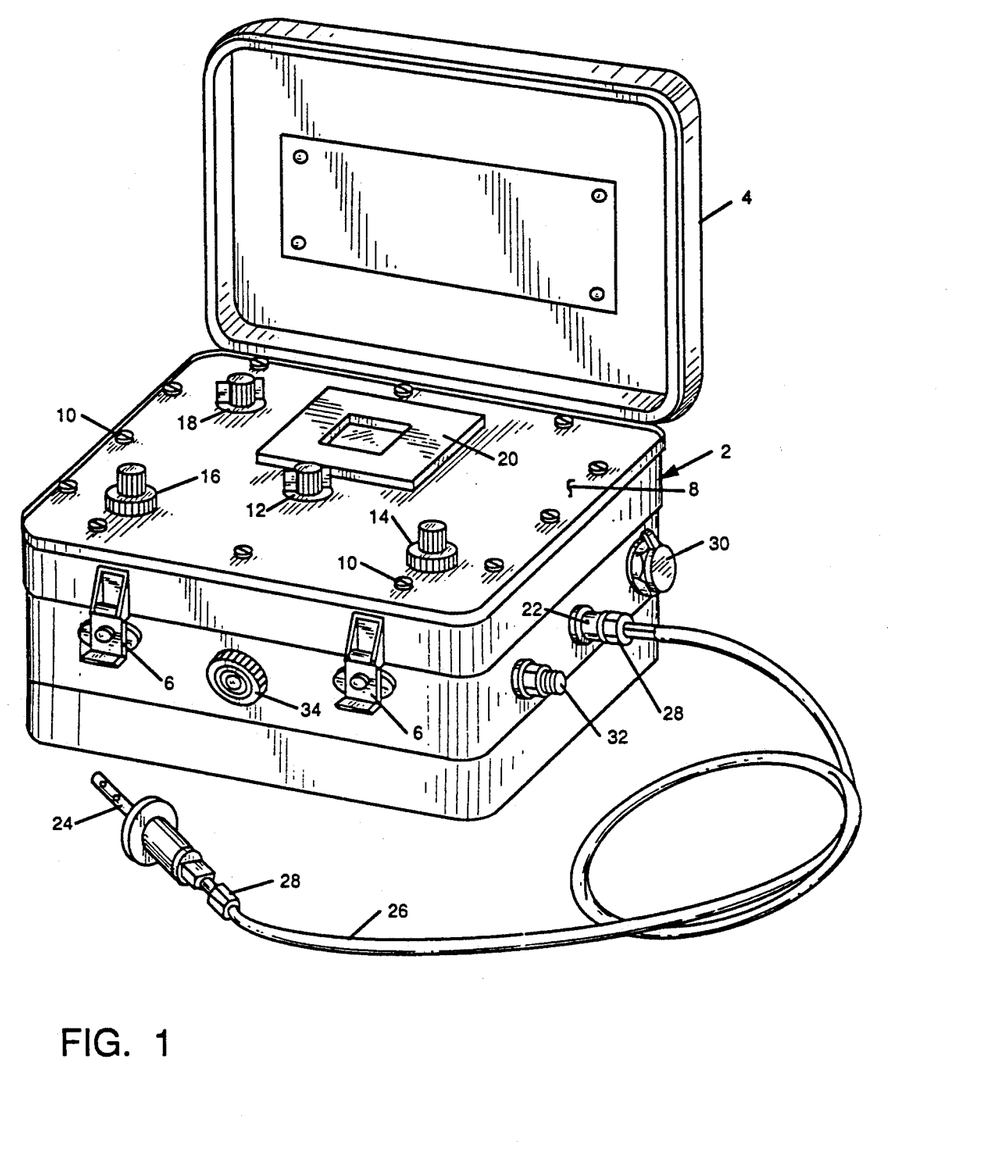
FIG. 1 is a perspective view of one embodiment of a multiple K factor, selectable gas detector in accordance with the present invention.
Figure 2:
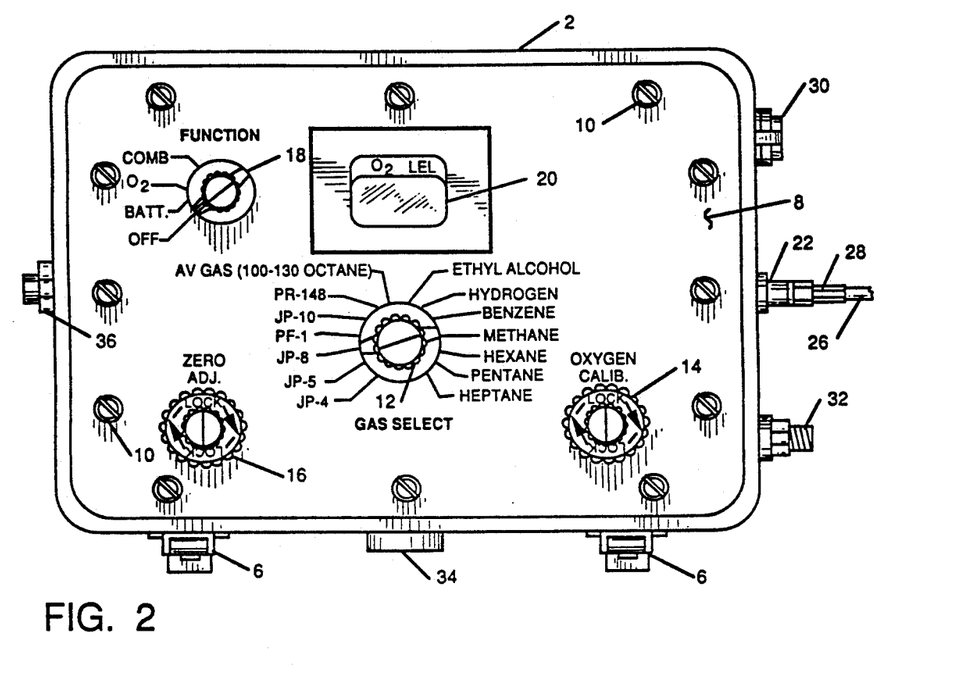
FIG. 2 is a top plan view of the gas detector shown in FIG. 1 with the cover removed.

One embodiment of a multiple K factor, selectable combustible gas detector in accordance with the present invention is shown in FIGS. 1 and 2. The gas detector includes a housing 2 which contains substantially all of the electronics, gas sensors and other operating mechanisms of the present invention. The housing 2 is preferably closed by a cover 4 hingedly connected thereto and capable of being locked in place on the housing 2 by a pair of latches 6 or the like. The upper portion of the housing 2 has a flat panel 8 mounted thereto by a plurality of panel screws 10 or the like. The panel 8 carries a variety of control switches and knobs, including a fourteen position gas select control switch 12, an oxygen sensor calibration control knob 14, a combustible gas sensor zero adjust control knob 16 and a four position function control switch 18. The panel also carries a visual display 20, such as a digital liquid crystal display. Since the present invention can selectively detect both oxygen and combustible gases, as dictated by the function control switch 18, the display 20 can provide readings of either the oxygen concentration or a percent of the lower explosive limit (LEL) of the combustible gas being detected. Other information can also be shown by the display 20, including, when the function control switch 18 is positioned appropriately, the status of an internal battery, an alarm indication or the like.

A gas inlet 22 is provided in one side of the housing 2 to the interior of the housing 2. Gas samples can be collected by a gas probe 24 and carried to the gas inlet 22 through an elongated hose 26 or the like. The hose 26 can be easily connected to the gas inlet 22 and gas probe 24, respectively, by quick-connect sockets 28 or the like. The side of the housing 2 carrying the gas inlet 22 can also include a battery charge terminal 30 and a ground terminal 32. The front of the housing 2 can include an audible alarm 34. As shown in FIG. 2, the side of the housing 2 opposite the gas inlet 22 can include an exhaust gas outlet 36 therethrough.

Figure 3:
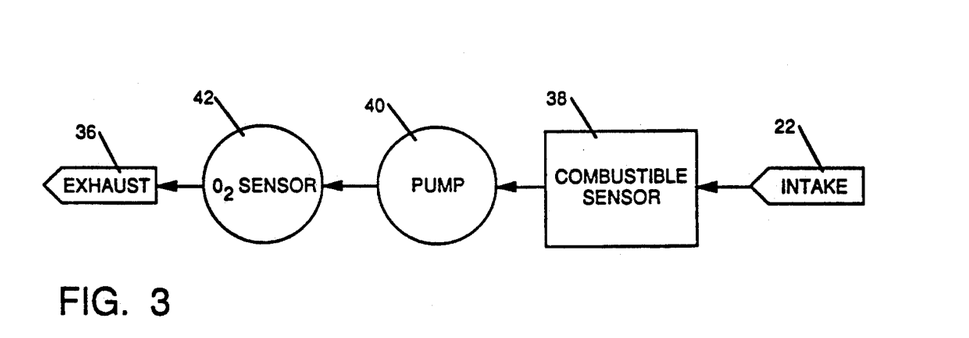
FIG. 3 is a block diagram showing the gas sample flow in the gas sensor shown in FIG. 1.

The flow of a gas sample through the gas detector of the present invention is shown schematically in FIG. 3. The gas sample enters the intake, e.g., the gas inlet 22, in the housing 2 and passes over a combustible sensor, such as combustible gas sensor 38, and through a pump 40 which draws the gas sample through the gas inlet 22. The gas sample then passes over an O₂ sensor, such as oxygen sensor 42, and is exhausted through the exhaust gas outlet 36 in the housing 2.

Figure 4A:
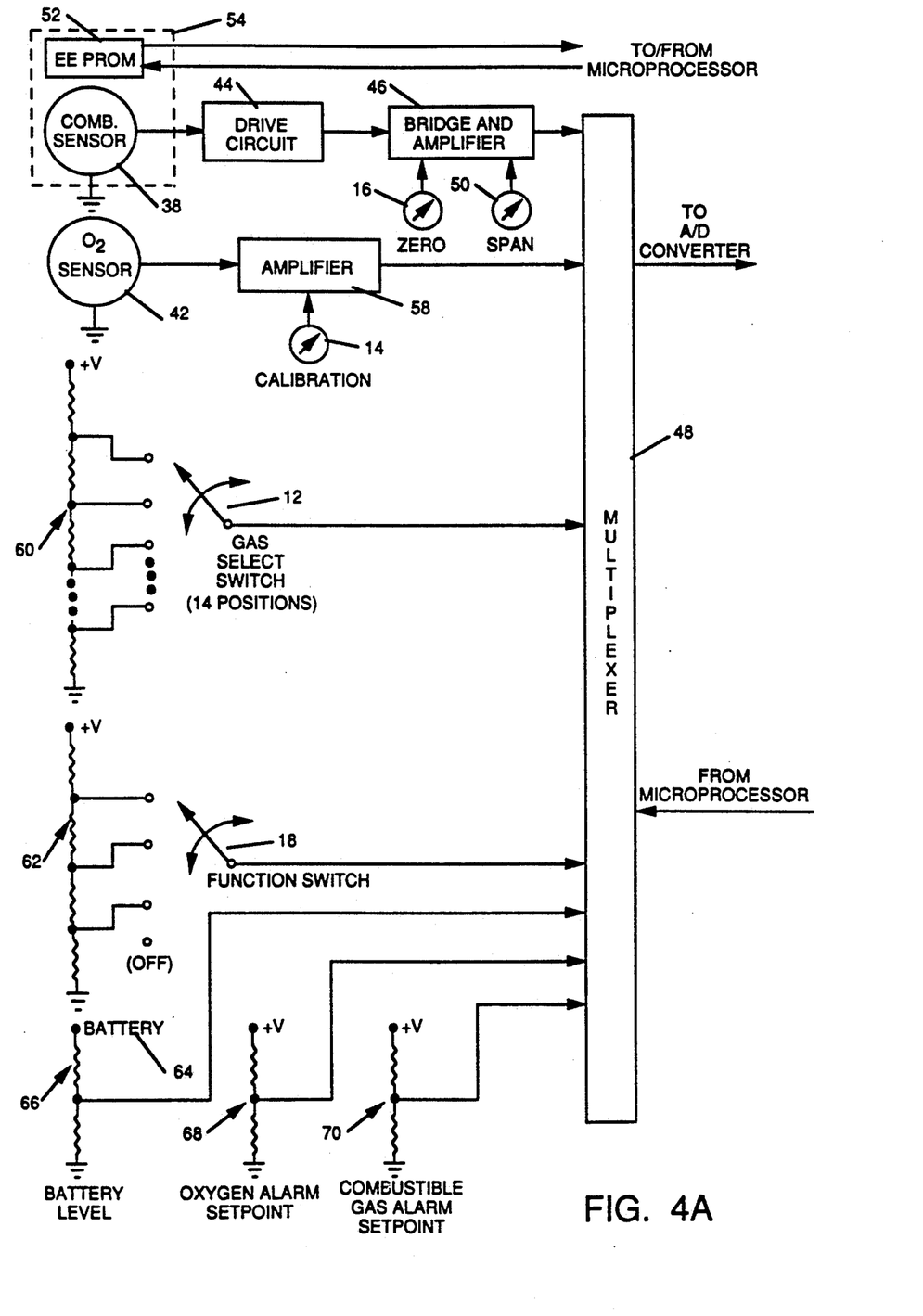
FIGS. 4A and 4B are block diagrams of the control and operating circuitry included in the gas detector shown in FIG. 1.
Figure 4B:
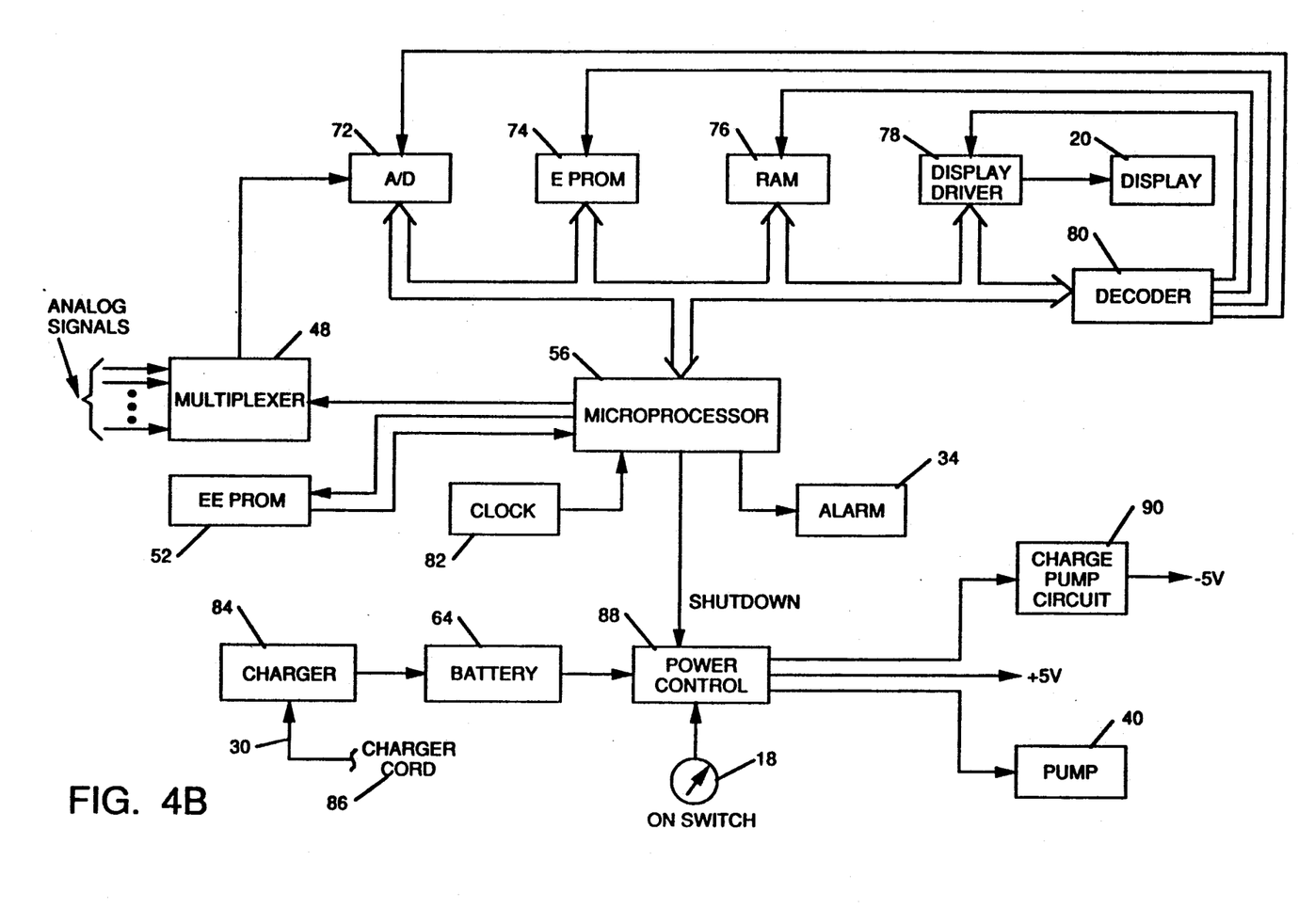

The major components of the operating and control circuitry of the gas detector of the present invention are shown in block diagram format in FIGS. 4A and 4B. The combustible gas sensor 38 generates a combustible gas output signal which is related to, and typically directly proportional to, the concentration of a combustible gas contacting the combustible gas sensor 38. The combustible gas sensor 38 is powered by a drive circuit 44 and electrical signals developed in the combustible gas sensor 38 are detected by a bridge and amplifier 46 which generates an analog electrical signal representing the concentration of the detected combustible gas. This amplified combustible gas output signal is supplied in analog form to a multiplexer 48. The bridge and amplifier circuit 46 for the combustible gas sensor 38 can be appropriately adjusted by the zero adjust control knob 16 on the panel 8 and by an internal span potentiometer 50. It is preferred that the drive circuit 44 maintain at least an active element of the combustible gas sensor 38 at a relatively constant temperature level during normal operation.

An electrically erasable programmable read only memory (EEPROM) 52, or other digital memory device, is closely associated with the combustible gas sensor 38, preferably the two devices are mounted on a common printed circuit board 54. The EEPROM 52 stores at least one K factor, unique to and generated by using the particular combustible gas sensor 38 associated therewith, for each of a plurality of predetermined combustible gases to be sensed by the gas detector. As will be explained in more detail hereinafter in connection with FIG. 4B, control signals for the EEPROM 52 are received from a microprocessor 56 and information stored in the EEPROM 52 is supplied to the microprocessor 56, all preferably in digital format.

The oxygen sensor 42, such as an electrochemical oxygen sensor, generates an oxygen output signal which is proportional to the concentration of oxygen in the gas sample. This electrical output signal generated by the oxygen sensor 42 is enhanced in an oxygen sensor amplifier 58 and supplied to the multiplexer 48 in analog format. The oxygen sensor amplifier 58 can be calibrated by the oxygen calibration control knob 14 located on the panel 8 of the housing 2.

The gas select control switch 12, which is also mounted on the panel 8, provides a unique analog electrical signal to the multiplexer 48 for each of the plurality of combustible gases which may be detected by the gas detector. One arrangement for providing the varying analog signals from the gas select control switch 12 is shown in FIG. 4A. A gas select series resistance network 60 is connected between a source of voltage and ground to provide a voltage divider arrangement. Each contact of the illustrated multi-position gas select control switch 12 is connected to a point between different adjacent pairs of resistors in the gas select resistance network 60. Therefore, each position of the gas select control switch 12 selected will provide to the multiplexer 48 a voltage of a unique magnitude. Similarly, the function control switch 18 provides a varying analog signal to the multiplexer 48 depending on the position of the function control switch 18. A function series resistance network 62 is connected between a source of voltage and ground. The contacts of the function control switch 18 are separately connected to points on the function resistance network 62 between different adjacent pairs of resistors therein.

An analog electrical signal representing the level of voltage in a battery 64 for the gas detector is supplied to the multiplexer 48 by tapping into a first voltage divider 66 connected between the battery and ground. Finally, a second voltage divider 68 and a third voltage divider 70, each connected between a source of voltage and ground, provide analog electrical signals at preselected or adjustable and unique levels to the multiplexer 48, and represent an oxygen alarm set point and a combustible gas alarm set point, respectively.

The analog signals generated by the various elements of the apparatus shown in FIG. 4A are preferably processed by a microprocessor based digital controller, which is shown in more detail in FIG. 4B. The microprocessor 56 is connected to and has two-way communication with an analog-to-digital (A/D) converter 72, an erasable programmable read only memory (EPROM) 74, a random access memory (RAM) 76, a display driver 78 and a decoder 80. The decoder 80 also has control lines connected, in turn, to the A/D converter 72, EPROM 74, RAM 76 and display driver 78 to control their operation as directed by the microprocessor 56. In addition, the display driver 78 directly controls the display 20 carried by the panel 8 in the housing 2. A clock 82 provides necessary timing information for the operation of the microprocessor 56. For ease of use and convenience, it is preferred that the apparatus be portable and operated by the battery 64 as shown in FIG. 4B, although other sources of electrical power can also be used. The battery 64 can be charged by a standard charger 84 which is connected by a charger cord 86 extending from the battery charge terminal 30 of the housing 2 to any standard alternating or direct current power supply. The battery 64 supplies its voltage to a power control 88 which, in response to an "on" signal, i.e., movement of the function control switch 18 from the "off" position, supplies power to the pump 40 and generates a positive five volt signal used in various of the electronic elements. The power control 88 is also connected to a charge pump circuit 90 which generates a negative five volt power supply. In the event that certain failures are detected in the system, the microprocessor 56 can supply a shutdown signal to the power control circuit 88. Finally, the microprocessor 56, also in response to certain detected conditions, can activate the audible alarm 34 carried by the housing 2 as well as generate an appropriate signal for the display 20.

Referring to both FIGS. 4A and 4B, it can be seen that the analog signals collected by the multiplexer 48 are supplied directly to the A/D converter 72 and the microprocessor 56 also supplies control signals to the multiplexer 48 to control the input, typically in serial fashion, of these analog signals into the A/D converter 72. The processor circuit operates in response to the various signals supplied thereto through the multiplexer 48 and by using predetermined and known processes or equations stored in the EPROM 74, random access memory 76, or microprocessor 56, performs various calculations on the analog signals and generates appropriate displays, alarms, warnings or the like in the gas detector.

Of primary interest in the present invention is the generation of oxygen concentration signals and combustible gas concentration signals as determined from the oxygen sensor 42 and the combustible gas sensor 38 measuring the gas sample provided thereto. If the function control switch 18 is moved to the oxygen detecting mode or position, then the signal from the oxygen sensor 42 will be analyzed by the processor circuit and the display 20 will indicate the concentration of oxygen in the gas sample. Based upon the setting provided by the alarm oxygen set point, an alarm will be indicated if the concentration of oxygen falls below a predetermined level.

If the function control switch 18 is moved to the combustible gas detection position or mode, then the processor circuit will analyze the signal from the combustible gas sensor 38 and provide an appropriate reading, shown on the display 20, for the concentration of the combustible gas in the gas sample. The position of the gas select control switch 12 will inform the processor circuit of the particular predetermined combustible gas which is being sought. The microprocessor 56 will then, in response to the position of the gas select control switch 12, instruct the EEPROM 52 to provide the microprocessor 56 with the appropriate K factor stored therein for that particular selected gas. If more than one K factor is assigned to a particular selected combustible gas, then all of the K factors for that gas will be supplied to the microprocessor 56. The microprocessor 56 will then perform the appropriate calculations on the received data and the supplied K factor or K factors to generate a signal representing the concentration of the combustible gas detected in the gas sample by the combustible gas sensor 38. This signal will then be shown on the display 20 on the panel 8.

In the present invention, it is preferred that the combustible gas concentration reading on the display 20 be given as a percent of the lower explosive limit of the combustible gas. However, other concentration readings can be given, such as actual concentration in parts per million, percent of gas by volume, or the like. It is relatively straightforward to convert from one concentration measure to another since they are interrelated by known constants for the various gases. Similarly to the oxygen alarm set point, the combustible gas alarm set point provides the microprocessor 56 with a lower limit of safety for any combustible gas. If the concentration of the detected combustible gas in the gas sample exceeds this set point, the audible alarm 34 is activated.

As is well known in the art, the K factor for a particular gas is generally unique to a gas for a particular construction of a sensor. The present invention detects a plurality of gases using only a single gas sensor. The various K factors for the gases are not calculated in advance and stored uniformly in each detector and used without change in all future measurements. Rather, recognizing the inherent differences in output response from individual sensor to individual sensor, the various K factors for each gas are determined based upon a particular and unique individual gas sensor to be used with the present detector arrangement. In other words, the EEPROM associated with the gas sensor includes at least one K factor for each of the plurality of gases, and the K factors are unique to and are generated by using the particular gas sensor associated with the EEPROM.

There are many known ways for generating K factors for a particular gas and for a particular gas sensor. In accordance with the preferred method used in the present invention, the particular combustible gas sensor 38 in question is first subjected to electrical power at an appropriate level to enable the gas sensor to operate in its normal, intended mode. With clean air, i.e., air with a zero concentration of any of the combustible gases, applied to the combustible gas sensor 38, the electrical output generated by the combustible gas sensor 38 is measured. Then, one of the predetermined combustible gases in at least one known concentration is applied to the combustible gas sensor 38 and the electrical output generated thereby is measured. The K factor for this gas and for this particular sensor is then calculated based upon the measured electrical readings and the known concentration of the first combustible gas. These same calculation steps are repeated using the others of the predetermined combustible gases in known concentrations and calculating the K factors. The K factors are then stored in the EEPROM 52 for future use. The EEPROM 52 and combustible gas sensor 38 are preferably carried on a common printed circuit board 54 so that the particular combustible gas sensor 38 and EEPROM 52 containing unique information for that gas sensor remain together. Ideally, the EEPROM 52/ gas sensor 38 package is calibrated with the various K factors at a central location so that any such package can be readily inserted into any of the gas detectors using this arrangement.

In the simplest arrangement for calibrating the EEPROM 52/combustible gas sensor 38 package, one known concentration of each of the predetermined combustible gases is sequentially applied to the combustible gas sensor 38 and the electrical readings taken therefrom for determining the K factors. In addition, it is assumed that the response of the combustible gas sensor 38 for each combustible gas is linear and that one K factor for each combustible gas would be sufficient. However, it is apparent to one skilled in the art that other arrangements can be used. For example, more than one K factor can be determined for each gas across a range of concentrations. Non-linear curves can be fit to the calculated data to generate a function curve for the K factor for each gas. In addition, one can assume that the combustible gas sensor 38 operates linearly, but apply a test combustible gas at more than one known concentration to generate more than one K factor. The multiple K factors for that particular gas could be averaged together to generate the single K factor used for tests of unknown gas concentrations.

One example of the actual calculation of K factors for a catalytic combustible gas sensor is set forth below in conjunction with Table I.

TABLE I

| % LEL/Gas | Va | Vr | Va-Vr | Signal | Sensitivity | K Factor |
|---|---|---|---|---|---|---|
| 0 | 1.9080 | 1.9380 | −0.0300 | | | |
| 50 CH4 | 1.7168 | 1.5590 | 0.1578 | 0.1878 | 3.756 | 1.0000 |
| 0 | 1.9076 | 1.9352 | −0.0276 | | | |
| 50 H2 | 1.6770 | 1.4851 | 0.1919 | 0.2195 | 4.390 | 0.8556 |
| 0 | 1.9079 | 1.9353 | −0.0274 | | | |
| 25 H2 | 1.7990 | 1.7079 | 0.0911 | 0.1185 | 4.740 | 0.7924 |
| 0 | 1.9079 | 1.9353 | −0.0274 | | | |
| 53.3 HEX | 1.8028 | 1.7249 | 0.0779 | 0.1053 | 1.976 | 1.9012 |

TABLE I-continued

| % LEL/Gas | Va | Vr | Va-Vr | Signal | Sensitivity | K Factor |
|---|---|---|---|---|---|---|
| 0 | 1.9076 | 1.9350 | −0.0274 | | | |
| 22.8 HEX | 1.8630 | 1.8428 | 0.0202 | 0.0476 | 2.088 | 1.7991 |
| 0 | 1.9077 | 1.9348 | −0.0271 | | | |
| 47.3 HEP | 1.8315 | 1.7790 | 0.0525 | 0.0796 | 1.683 | 2.2319 |
| 0 | 1.9075 | 1.9350 | −0.0275 | | | |
| 17.5 HEP | 1.8790 | 1.8762 | 0.0028 | 0.0303 | 1.731 | 2.1693 |
| 0 | 1.9074 | 1.9351 | −0.0277 | | | |
| 46.8 PEN | 1.7839 | 1.6898 | 0.0941 | 0.1218 | 2.603 | 1.4432 |
| 0 | 1.9075 | 1.9352 | −0.0277 | | | |
| 19.7 PEN | 1.8594 | 1.8348 | 0.0246 | 0.0523 | 2.655 | 1.4148 |
| 0 | 1.9079 | 1.9353 | −0.0274 | | | |
| 48.4 BEN | 1.7878 | 1.6978 | 0.0900 | 0.1174 | 2.426 | 1.5485 |
| 0 | 1.9068 | 1.9339 | −0.0271 | | | |
| 19.4 BEN | 1.8610 | 1.8408 | 0.0202 | 0.0473 | 2.438 | 1.5405 |
| 0 | 1.8477 | 1.8626 | −0.0149 | | | |
| 28.6 PR148 | 1.7889 | 1.7500 | 0.0389 | 0.0538 | 1.881 | 1.9967 |
| 0 | 1.8509 | 1.8663 | −0.0154 | | | |
| 28.6 JP-4 | 1.8086 | 1.7758 | 0.0328 | 0.0482 | 1.685 | 2.2287 |
| 0 | 1.8520 | 1.8717 | −0.0197 | | | |
| 28.6 JP-10 | 1.8148 | 1.7983 | 0.0165 | 0.0362 | 1.266 | 2.9674 |
| 0 | 1.8519 | 1.8735 | −0.0216 | | | |
| 28.6 PF-1 | 1.8130 | 1.7964 | 0.0166 | 0.0382 | 1.336 | 2.8121 |
| 0 | 1.8509 | 1.8713 | −0.0204 | | | |
| 28.6 ETHYL | 1.7740 | 1.7230 | 0.0510 | 0.0714 | 2.497 | 1.5045 |
| 0 | 1.8502 | 1.8741 | −0.0239 | | | |
| 22.2 JP-8 | 1.8170 | 1.8079 | 0.0091 | 0.0330 | 1.486 | 2.5268 |
| 0 | 1.8532 | 1.8697 | −0.0165 | | | |
| 28.6 JP-5 | 1.8199 | 1.8083 | 0.0116 | 0.0281 | 0.983 | 3.8228 |
| 0 | 1.8532 | 1.8697 | −0.0165 | | | |
| 28.6 AVGAS | 1.7933 | 1.7495 | 0.0438 | 0.0603 | 2.108 | 1.7815 |

The particular combustible gas sensor used in developing Table I included an active resistive element covered with a catalytic material and a reference resistive element not covered with the catalytic material. Both the active and the reference resistance elements were subjected to the gas sample and were subjected to an appropriate electrical voltage. The first column in Table I represents the particular gas and the concentration of the gas applied, as given in percent of the lower explosive limit for the gas. For example, the second entry in the first column of Table I shows that methane ($CH_4$) at a concentration of 50% of its LEL was applied to the gas sensor. Readings were taken of the voltages (in volts) across the active and reference elements (Va, Vr) in the second and third columns, respectively, and a difference in these readings (Va-Vr) is shown in the fourth column of Table I. In addition, in the column labeled "signal", the difference (in volts) between Va and Vr with the test gas applied compared to the difference between Va and Vr when no gas is applied is given. The sensitivity (in millivolts per LEL) is shown in the sixth column as the ratio of the "Signal" divided by the concentration of the gas applied.

The sensitivity for each gas as calculated above can be used directly as the K factor for future measurements. However, applicants have found it advantageous to arbitrarily assign one of the gases (the reference gas) a K factor of 1 and to compute the K factors for the remaining gases relative to the reference gas. In the example shown in Table I, methane has been assigned a K factor of 1 and the K factor for hydrogen has been computed as the ratio of the measured sensitivity of the gas sensor to methane to the measured sensitivity of the gas sensor to hydrogen. This method of determining the K factors can be shown by the following calculations for methane and hydrogen, based upon the readings set forth in Table I:

Methane Signal = (Va-Vr with test gas) − (Va-Vr with zero gas)
= 0.1578 v − (−0.0300 v)
= 0.1878 volts Methane Sensitivity = $\frac{\text{Methane signal}}{\text{concentration applied}}$ = $\frac{0.1878 \text{ volts}}{50} \times 1000$ mv/volt = 3.756 mv/% LEL Hydrogen Signal = (Va-Vr with test gas) − (Va-Vr with zero gas)
= 0.1919 v − (−0.0276 v)
= 0.2195 volts Hydrogen Sensitivity = $\frac{\text{Hydrogen signal}}{\text{concentration applied}}$ = $\frac{0.2195 \text{ volts}}{50} \times 1000$ mv/volt = 4.390 mv/% LEL Hydrogen K Factor = $\frac{\text{Methane sensitivity}}{\text{hydrogen sensitivity}}$ = $\frac{3.756}{4.390}$

= 0.8556

The same calculations are made for each of the other gases shown in Table I, using the appropriate voltage readings, to determine the remaining K factors shown therein in the column identified as "K Factor". These K factors are then stored in the EEPROM 52 and used in future operations with that particular gas sensor. Table I also shows that several of the gases, including hexane, heptane, pentane and benzyne, had different K factors calculated at different gas concentrations. For these gases, an average of the two K factors would be used in future calculations, assuming linearity of gas response.

Figure 5:
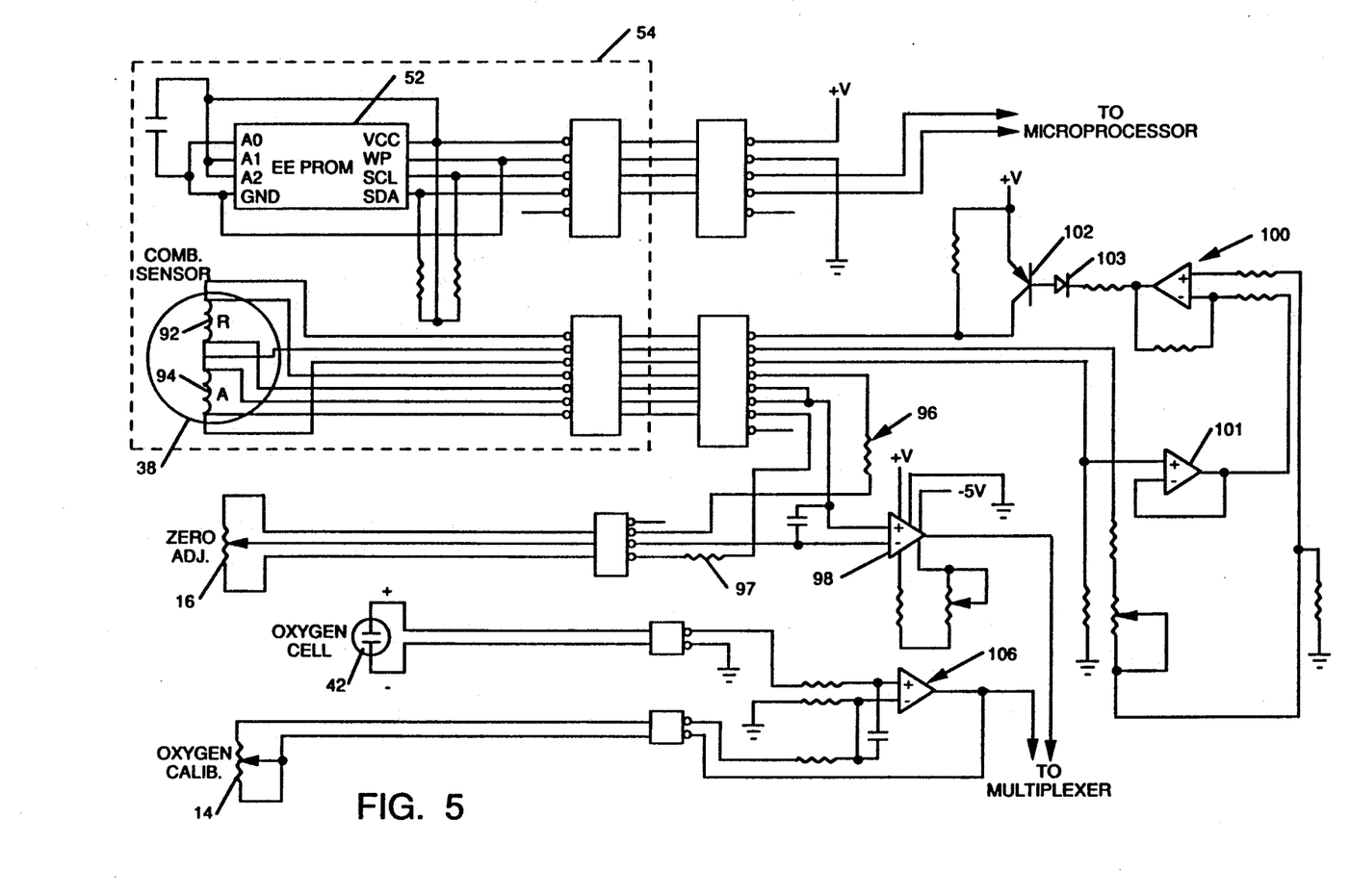
FIG. 5 is a schematic drawing of the electronics controlling the combustible gas sensor and oxygen sensor in the gas detector of FIG. 1.

FIG. 5 shows a circuit diagram of a preferred arrangement of the elements powering and controlling the combustible gas sensor 38, EEPROM 52 and oxygen sensor 42 previously described. The combustible gas sensor 38 is preferably a catalytic type of sensor having a reference element 92 and an active element 94. The EEPROM 52 shown in FIG. 5 is a Model No. 24CO4 manufactured by Exar Company, but other EEPROMs or other digital memory devices can also be used. The EEPROM 52 and combustible gas sensor 38 are mounted on a common printed circuit board 54. The combustible gas sensor 38 is preferably inserted as one leg of a Wheatstone bridge which also includes resistors 96 and 97. The zero adjustment for the combustible gas sensor 38 is provided by a potentiometer in the zero adjust control knob 16 connected into the bridge. The electrical signal developed by the combustible gas sensor 38 is increased in amplifier 98 and supplied to the multiplexer 48. The circuit consisting of amplifiers 100, 101 and transistor 102, along with the associated resistors and a diode 103 between transistor 102 and amplifier 100, are arranged as a constant temperature circuit to maintain at least the active element 94 of the combustible gas sensor 38 in a constant temperature mode of operation. The details of the operation of such a constant temperature circuit are known as shown, for example, in U.S. Pat. No. 4,541,988, the disclosure of which is incorporated herein by reference. Finally, the signal developed by the oxygen sensor 42 is increased by amplifier 106 and supplied to the multiplexer 48. The calibration for the oxygen cell is provided by a potentiometer in the oxygen calibration control knob 14 connected to the circuit for amplifier 106.

Having described the presently preferred embodiments of the present invention, it is to be understood that the invention may be otherwise embodied within the scope of the appended claims.

I claim:

1. Gas detecting apparatus for determining the concentration, in a gas sample, of a selected one of a plurality of predetermined gases, said apparatus comprising:
    sampling means for obtaining said gas sample;
    a single gas sensor connected to said sampling means for generating a gas output signal related to the concentration of said selected predetermined gas in said gas sample;
    drive means for supplying controlled electrical power to said gas sensor;
    K factor storage means associated with said gas sensor for storing at least one K factor, unique to and generated by using said gas sensor, for each of said plurality of predetermined gases;
    gas selector means for generating a selected gas signal representing the particular selected gas to be detected;
    a processor means for selecting, in response to the selected gas signal and gas output signal, the K factor or factors from said K factor storage means for the selected gas and for calculating, in accordance with a predetermined process stored in said processor means, a concentration signal representing the concentration of the selected gas in said gas sample; and
    display means responsive to said concentration signal for displaying the concentration of said gas to be detected in said gas sample.

2. The gas detecting apparatus of claim 1 wherein said gas sensor is a combustible gas sensor.

3. The gas detecting apparatus of claim 2 wherein said combustible gas sensor is a catalytic combustible gas sensor having an active element and a reference element, each of whose resistance varies as a function of temperature, with said sensor forming one branch of a Wheatstone bridge network, and with electrical imbalances in said bridge generating said gas output signal.

4. The gas detecting apparatus of claim 3 wherein said drive means adjusts the electrical power supplied to said catalytic combustible gas sensor to maintain the operating temperature of at least said active element at a predetermined constant level.

5. The gas detecting apparatus of claim 1 further including alarm means for indicating when the concentration of a particular gas in said gas sample exceeds a predetermined level.

6. The gas detecting apparatus of claim 1 wherein said processor means is a microprocessor based digital controller.

7. The gas detecting apparatus of claim 6 wherein the gas output signal and the selected gas signal are analog signals which are supplied to a multiplexer which supplies these signals to an analog-to-digital converter in said digital controller, and wherein the K factor storage means is a digital memory means supplying its stored K factor information directly to a microprocessor in said digital controller.

8. The gas detecting apparatus of claim 7 wherein said digital memory means is an electrically erasable programmable read only memory.

9. The gas detecting apparatus of claim 7 wherein said gas selector means is formed of a series resistance network connected to a source of voltage and includes a plurality of contacts positioned between adjacent resistors in said resistance network and connected to a multi-position selector switch having at least as many positions as the number of predetermined gases to be selected.

10. The gas detecting apparatus of claim 1 wherein said gas sensor and said K factor storage means are mounted on a common support.

11. The gas detecting apparatus of claim 1 wherein the K factors stored in said K factor storage means are generated in advance for a particular gas sensor in accordance with the following steps:
    a. applying electrical power to said gas sensor;
    b. measuring the gas output signal when clean air is applied to said gas sensor;
    c. applying a first of said predetermined gases in a known concentration to said gas sensor and measuring the gas output signal generated thereby;
    d. calculating the K factor of said first gas based upon the gas output signals generated in steps (b) and (c) above and the known concentration of said first gas; and
    e. repeating steps (b) through (d) for each of the remaining of said predetermined gases.

12. The gas detecting apparatus of claim 11 wherein one of said gases is selected as a reference gas and assigned a K factor of 1, and wherein the K factors for each of the remaining gases are calculated with respect to the reference gas.

13. Gas detecting apparatus for determining the concentration, in a gas sample, of a selected one of a plurality of predetermined combustible gases, said apparatus comprising:

sampling means for obtaining said gas sample;

a single combustible gas sensor connected to said sampling means for generating a combustible gas output signal related to the concentration of said selected predetermined combustible gas in said sample;

drive means for supplying controlled electrical power to said combustible gas sensor;

K factor storage means associated with said combustible gas sensor for storing at least one K factor, unique to and generated by using said combustible gas sensor, for each of said plurality of predetermined combustible gases;

gas selector means for generating a selected gas signal representing the particular selected combustible gas to be detected;

a processor means for selecting, in response to the selected gas signal and combustible gas output signal, the K factor or factors from said K factor storage means for the selected combustible gas in said gas sample; and display means responsive to said concentration signal for displaying the concentration of said combustible gas to be detected in said gas sample.

14. The gas detecting apparatus of claim 13, wherein said combustible gas sensor is a catalytic combustible gas sensor.

15. The gas detecting apparatus of claim 14 wherein said catalytic combustible gas sensor has an active element and a reference element, each of whose resistance varies as a function of temperature, with said sensor forming one branch of a Wheatstone bridge network, and with electrical imbalances in said bridge generating said combustible gas output signal.

16. The gas detecting apparatus of claim 15 wherein said drive means adjusts the electrical power supplied to said catalytic combustible gas sensor to maintain the operating temperature of at least said active element at a predetermined constant level.

17. The gas detecting apparatus of claim 13 further including alarm means for indicating when the concentration of a particular combustible gas in said gas sample exceeds a predetermined level.

18. The gas detecting apparatus of claim 13 wherein said processor means is a microprocessor based digital controller.

19. The gas detecting apparatus of claim 18 wherein the combustible gas output signal and the selected gas signal are analog signals which are supplied to a multiplexer which supplies these signals to an analog-to-digital converter in said digital controller, and wherein the K factor storage means is a digital memory means supplying its stored K factor information directly to a microprocessor in said digital controller.

20. The gas detecting apparatus of claim 19 wherein said digital memory means is an electrically erasable programmable read only memory.

21. The gas detecting apparatus of claim 19 wherein said gas selector means is formed of a series resistance network connected to a source of voltage and includes a plurality of contacts positioned between adjacent resistors in said resistance network and connected to a multi-position selector switch having at least as many positions as the number of predetermined combustible gases to be selected.

22. The gas detecting apparatus of claim 13 wherein said combustible gas sensor and said K factor storage means are mounted on a common support.

23. The gas detecting apparatus of claim 13 wherein the K factors stored in said K factor storage means are generated in advance for a particular combustible gas sensor in accordance with the following steps:
 a. applying electrical power to said combustible gas sensor;
 b. measuring the combustible gas output signal when no gas is applied to said combustible gas sensor;
 c. applying a first of said predetermined combustible gases in a known concentration to said combustible gas sensor and measuring the combustible gas output signal generated thereby;
 d. calculating the K factor of said first combustible gas based upon the combustible gas output signals generated in steps (b) and (c) above and the known concentration of said first combustible gas; and
 e. repeating steps (b) through (d) for each of the remaining of said predetermined combustible gases.

24. The gas detecting apparatus of claim 23 wherein one of said combustible gases is selected as a reference gas and assigned a K factor of 1, and wherein the K factors for each of the remaining combustible gases are calculated with respect to the reference gas.

25. The gas detecting apparatus of claim 13 wherein the concentration signal represents a percent of the lower explosive limit of said selected combustible gas in said gas sample.

26. Gas detecting apparatus for determining the concentration, in a gas sample, of a selected one of a plurality of predetermined combustible gases, said apparatus comprising:

sampling means for obtaining said gas sample;

a single combustible gas sensor connected to said sampling means for generating a combustible gas output signal related to the concentration of said selected predetermined combustible gas in said gas sample;

drive means for supplying controlled electrical power to said combustible gas sensor;

an oxygen sensor connected to said sampling means for generating an oxygen output signal proportional to the concentration of oxygen in said gas sample;

K factor storage means associated with said combustible gas sensor for storing at least one K factor, unique to and generated by using said combustible gas sensor, for each of said plurality of predetermined combustible gases;

gas selector means for generating a selected gas signal representing the particular selected combustible gas to be detected;

a mode selector means for generating a mode signal representing the mode of operation of said apparatus, with said mode selector means selectable between at least an oxygen detection mode and a combustible gas detection mode;

a processor means for (i) in response to the mode signal, selected gas signal, combustible gas output signal and oxygen output signal, and using predetermined processes stored in said processor means, calculating a first concentration signal representing the concentration of oxygen detected in said gas sample, or (ii) selecting the K factor or factors from said K factor storage means for the selected combustible gas and calculating a second concentration signal representing the concentration of the selected combustible gas in said gas sample; and display means responsive to said first and second concentration signals for displaying, as determined by the mode signal, either the concentration of oxygen to be detected in said gas sample or the concentration of combustible gas to be detected in said gas sample.

27. The gas detecting apparatus of claim 26 wherein said oxygen sensor is an electrochemical oxygen sensor.

28. The gas detecting apparatus of claim 26 wherein said combustible gas sensor is a catalytic combustible gas sensor.

29. The gas detecting apparatus of claim 28 wherein said catalytic combustible gas sensor has an active element and a reference element, each of whose resistance varies as a function of temperature, with said sensor forming one branch of a Wheatstone bridge network, and with electrical imbalances in said bridge generating said combustible gas output signal.

30. The gas detecting apparatus of claim 29 wherein said drive means adjusts the electrical power supplied to said catalytic combustible gas sensor to maintain the operating temperature of at least the active element at a predetermined constant level.

31. The gas detecting apparatus of claim 26 further including alarm means for indicating when the concentration of a particular combustible gas in said gas sample exceeds a predetermined level or when the concentration of the oxygen in said gas sample falls below a predetermined level.

32. The gas detecting apparatus of claim 26 wherein said processor means is a microprocessor based digital controller.

33. The gas detecting apparatus of claim 32 wherein the combustible gas output signal, selected gas signal, oxygen output signal and mode signal are analog signals which are supplied to a multiplexer which supplies these signals to an analog-to-digital converter in said digital controller, and wherein the K factor storage means is a digital memory means supplying its stored K factor information directly to a microprocessor in said digital controller.

34. The gas detecting apparatus of claim 33 wherein said digital memory means is an electrically erasable programmable read only memory.

35. The gas detecting apparatus of claim 33 wherein said gas selector means and said mode selector means are each formed of a series resistance network connected to a source of voltage and include a plurality of contacts positioned between adjacent resistors in said resistance network and connected to a multi-position selector switch having at least as many positions as the number of predetermined combustible gases or modes of operation, respectively, to be selected.

36. The gas detecting apparatus of claim 26 wherein said combustible gas sensor and said K factor storage means are mounted on a common support.

37. The gas detecting apparatus of claim 26 wherein the K factors stored in said K factor storage means are generated in advance for a particular combustible gas sensor in accordance with the following steps:

a. applying electrical power to said combustible gas sensor;

b. measuring the combustible gas output signal when clean air is applied to said combustible gas sensor;

c. applying a first of said predetermined combustible gases in a known concentration to said combustible gas sensor and measuring the combustible gas output signal generated thereby;

d. calculating the K factor of said first combustible gas based upon the combustible gas output signals generated in steps (b) and (c) above and the known concentration of said first combustible gas; and e. repeating steps (b) through (d) for each of the remaining of said predetermined combustible gases.

38. The gas detecting apparatus of claim 37 wherein one of said combustible gases is selected as a reference gas and assigned a K factor of 1, and wherein the K factors for each of the remaining combustible gases are calculated with respect to the reference gas.

39. The gas detecting apparatus of claim 26 wherein said first concentration signal represents a percent of the lower explosive limit of said selected combustible gas in said gas sample.

40. Gas detecting apparatus for determining the concentration, in a gas sample, of a selected one of a plurality of predetermine combustible gases, said apparatus comprising:

sampling means for obtaining said gas sample;

a single combustible gas sensor connected to said sampling means for generating a combustible gas output signal related to the concentration of said selected predetermined combustible gas in said gas sample;

drive means for supplying controlled electrical power to said combustible gas sensor;

an oxygen sensor connected to said sampling means for generating an oxygen output signal proportional to the concentration of oxygen in said gas sample;

K factor storage means associated with said combustible gas sensor for storing at least one K factor, unique to and generated by using said combustible gas sensor, for each of said plurality of predetermined combustible gases;

gas selector means for generating a selected gas signal representing the particular selected combustible gas to be detected;

a mode selector means for generating a mode signal representing the mode of operation of said apparatus, with said mode selector means selectable between at least an oxygen detection mode and a combustible gas detection mode;

a processor means for (i) in response to the mode signal, selected gas signal, combustible gas output signal and oxygen output signal, and using predetermined processes stored in said processor means, calculating a first concentration signal representing the concentration of oxygen detected in said gas sample, or (ii) selecting the K factor or factors from said K factor storage means for the selected combustible gas and calculating a second concentration signal representing the concentration of the selected combustible gas in said gas sample; and display means responsive to said first and second concentration signals for displaying, as determined by the mode signal, either the concentration of oxygen to be detected in said gas sample or the concentration of combustible gas to be detected in said gas sample, wherein the K factors stored in said K factor storage means are generated in advance for a particular combustible gas sensor in accordance with the following steps:

a. applying electrical power to said combustible gas sensor;

b. measuring the combustible gas output signal when clean air is applied to said combustible gas sensor;

c. applying a first of said predetermined combustible gases in a known concentration to said combustible gas sensor and measuring the combustible gas output signal generated thereby;

d. calculating the K factor of said first combustible gas based upon the combustible gas output signals generated in steps (b) and (c) above and the known concentration of said first combustible gas; and e. repeating steps (b) through (d) for each of the remaining of said predetermined combustible gases.

41. The gas detecting apparatus of claim 40 wherein said combustible gas sensor is a catalytic combustible gas sensor.

42. The gas detecting apparatus of claim 41 wherein said catalytic combustible gas sensor has an active element and a reference element, each of whose resistance varies as a function of temperature, with said sensor forming one branch of a Wheatstone bridge network, and with electrical imbalances in said bridge generating said combustible output signal, and with said drive means adjusting the electrical power supplied to said catalytic combustible gas sensor to maintain the operating temperature of at least the active element at a predetermined constant level.

43. The gas detecting apparatus of claim 40 wherein said processor means is a microprocessor based digital controller.

44. The gas detecting apparatus of claim 43 wherein the combustible gas output signal, selected gas signal, oxygen output signal and mode signal are analog signals which are supplied to a multiplexer which supplies these signals to an analog-to-digital converter in said digital controller, and wherein the K factor storage means is a digital memory means supplying its stored K factor information directly to a microprocessor in said digital controller.

45. The gas detecting apparatus of claim 44 wherein said digital memory means is an electrically erasable programmable read only memory.

46. The gas detecting apparatus of claim 44 wherein said gas selector means and said mode selector means are each formed of a series resistance network connected to a source of voltage and include a plurality of contacts positioned between adjacent resistors in said resistance network and connected to a multi-position selector switch having at least as many positions as the number of predetermined combustible gases or modes of operation, respectively, to be selected.

47. The gas detecting apparatus of claim 40 wherein said combustible gas sensor and said K factor storage means are mounted on a common support.

48. The gas detecting apparatus of claim 40 wherein said oxygen sensor is an electrochemical oxygen sensor.

49. The gas detecting apparatus of claim 40 further including alarm means for indicating when the concentration of a particular combustible gas in said gas sample exceeds a predetermined level or when the concentration of the oxygen in said gas sample falls below a predetermined level.

50. The gas detecting apparatus of claim 40 wherein one of said combustible gases is selected as a reference gas and assigned a K factor of 1, and wherein the K factors for each of the remaining combustible gases are calculated with respect to the reference gas.

51. The gas detecting apparatus of claim 40 wherein said first concentration signal represents a percent of the lower explosive limit of said selected combustible gas in said gas sample.

* * * * *

UNITED STATES PATENT AND TRADEMARK OFFICE
CERTIFICATE OF CORRECTION

PATENT NO. : 5,305,231
DATED : April 19, 1994
INVENTOR(S) : Mark J. Coppler, Robert L. Novack, John E. Tozier and Peter M. Noble It is certified that error appears in the above-indentified patent and that said Letters Patent is hereby corrected as shown below:

Column 7 Line 42 "Similarly" should read --Similar--.

Column 8 Line 53 "-that" should read --that--.

Column 9 Line 49 " "signal" " should read --"Signal"--.

Column 11 Line 40 "I" should read --We--.

Claim 13 Line 5 Column 13 after "said" insert --gas--.

Claim 13 Line 20 Column 13 after "gas" insert --and for calculating, in accordance with a predetermined process stored in said processor means, a concentration signal representing the concentration of the selected combustible gas--.

Claim 14 Line 25 Column 13 after "13" delete ",".

Claim 40 Line 18 Column 16 "predetermine" should read --predetermined--.

Signed and Sealed this

Thirtieth Day of August, 1994

Attest:

BRUCE LEHMAN

Attesting Officer

Commissioner of Patents and Trademarks